United States Patent [19]

Devoise-Lambert et al.

[11] Patent Number: 4,742,079
[45] Date of Patent: May 3, 1988

[54] FUNGICIDES CONTAINING CYMOXANIL AND METALAXYL

[75] Inventors: André Devoise-Lambert, Tagolsheim, France; Ulrich Gisi, Wenslingen, Switzerland

[73] Assignee: Sandoz Ltd., Basle, Switzerland

[21] Appl. No.: 936,879

[22] Filed: Dec. 2, 1986

Related U.S. Application Data

[62] Division of Ser. No. 827,584, Feb. 10, 1986, abandoned, which is a division of Ser. No. 689,137, Jan. 7, 1985, Pat. No. 4,585,763, which is a division of Ser. No. 459,761, Jan. 21, 1983, Pat. No. 4,507,310.

[30] Foreign Application Priority Data

Jan. 26, 1982 [GB] United Kingdom ............ 820215
Oct. 29, 1982 [GB] United Kingdom ............ 8231012

[51] Int. Cl.$^4$ ............ A01N 37/12; A01N 37/34; A01N 37/44
[52] U.S. Cl. ............ 514/528; 514/538
[58] Field of Search ............ 514/528, 538

[56] References Cited

U.S. PATENT DOCUMENTS 4,101,669 7/1978 Baude .................. 514/528
4,510,136 4/1985 Moberg ................. 514/63

FOREIGN PATENT DOCUMENTS 1500581 2/1978 United Kingdom .

OTHER PUBLICATIONS

Research Publication, Nov., 1979, pp. 632–633.
Phytopathology 71(5) 558(1981)–Abstract from Annual Meeting, Nov. 5–7, 1980.

Primary Examiner—Allen J. Robinson
Attorney, Agent, or Firm—Gerald D. Sharkin; Richard E. Vila

[57] ABSTRACT

The present invention relates to the use of a compound (a), an oomycetes controlling fungicide having the structure element of formula I

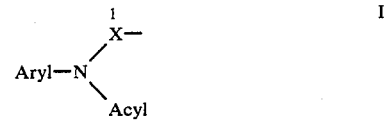

in which
 X is CH or N,
in association with
a compound (b), selected frm CYMOXANIL and Phosetyl-Al in combatting or preventing fungal diseases, and fungicidal composition comprising such compounds.

12 Claims, No Drawings

FUNGICIDES CONTAINING CYMOXANIL AND METALAXYL

This is a division of application Ser. No. 827,584, filed Feb. 10, 1986, now abandoned, which in turn is a division of application Ser. No. 689,137, filed Jan. 7, 1985, now issued as U.S. Pat. No. 4,585,763, which in turn is a division of application Ser. No. 459,761, filed Jan. 21, 1983, now issued as U.S. Pat. No. 4,507,310.

The present invention relates to fungicides, more particularly to oomycetes controlling fungicides.

Although a wide variety of fungicides including various oomycetes controlling fungicides are known, the need exists for still more effective fungicides.

It has been found that the use of (a) an oomycetes controlling fungicide having the structure element of formula I

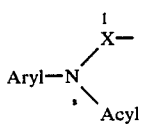

in which X is CH or N, in association with (b) a compound of formula II

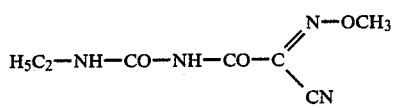

hereinafter referred to by the common name CYMOXANIL or of formula III

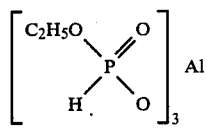

hereinafter referred to by the common name Phosetyl-Al is particularly effective in combatting or preventing fungal diseases.

Aryl, as used in formula I, is intended to embrace any aromatic radical, unsubstituted or substituted, e.g. phenyl unsubstituted or substituted.

Acyl, as used in formula I, is intended to embrace any organic radical tied by a CO-group to the N-atom.

An example of a group of oomycetes controlling fungicides having the structure element of formula I (hereinafter designated compounds of formula I) suitable for use in the invention are those of formula Ia

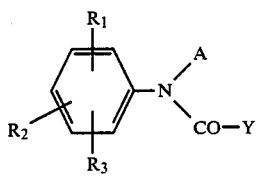

wherein $R_1$, $R_2$ and $R_3$, independently, are H, $C_{1-4}$alkyl, $C_{1-4}$alkoxy, $C_{1-4}$alkylthio or halogen selected from F, Cl and Br, A is selected from a group $-CH(R_4)-R_5$ or a group $-N(R_6)-COOR_7$, in which $R_4$ is H or $C_{1-4}$alkyl,

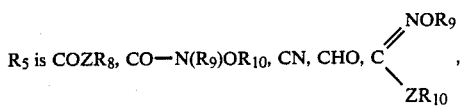

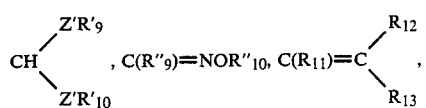

$C \equiv C-R_{14}$, allene; or is 2,2-dihalo-1-cyclopropyl unsubstituted or substituted by $C_{1-4}$-alkyl; or is phenyl unsubstituted or substituted.

$R_6$ is $C_{1-3}$alkyl, $R_7$ is $C_{1-6}$alkyl, $C_{3-6}$alkenyl or $C_{3-6}$alkinyl, whereby $R_6$ and $R_7$ may be linked together to form $CH_2-CH_2$; and wherein Z and Z' are O or S $R_8$ is $C_{1-6}$alkyl, $C_{3-6}$alkenyl, or $C_{3-6}$alkinyl, and whereby $ZR_8$ may be linked with $R_4$ to form the bridge $ZCH(R_{15})-CH_2$ in which Z is as defined above and $R_{15}$ is H or $CH_3$;

$R_9$, $R'_9$ and $R''_9$ are H or $C_{1-4}$alkyl, $R_{10}$, $R'_{10}$ and $R''_{10}$ are $C_{1-4}$alkyl, whereby $R_9$ may be linked with $R_{10}$, resp. $R'_9$ with $R'_{10}$, resp. $R''_9$ with $R''_{10}$ and signify alkylene, to form a 5- or 6-membered heterocyclic ring, $R_{11}$, $R_{12}$, $R_{13}$, independently, are H, $C_{1-4}$-alkyl, or halogen selected from F, Cl or Br, $R_{14}$ is H, $C_{1-4}$alkyl or halogen selected from Cl, Br or I, and Y is H;

a hydrocarbon selected from $C_{1-6}$alkyl, $C_{2-6}$alkenyl and $C_{2-6}$alkinyl unsubstituted or substituted by halogen, selected from F, Cl or Br, or by CN;

$C_{2-6}$epoxyalkylene; $C_{3-6}$cycloalkyl; a 5-membered heterocyclic ring comprising 1 to 3 heteroatoms selected from O, S and N, which is unsubstituted or substituted by $C_{1-4}$alkyl or halogen selected from F, Cl or Br;

$(A_1)_n-Az$; $(A_1)_n-Y_1-NR_{9a}R_{10a}$;

$(A_1)_nZ_1H$ and esters or ethers thereof;

benzyl unsubstituted or substituted, in which $A_1$ is $CH_2$ or $CH(CH_3)$ n is 0 or 1, Az is a 1-azolyl comprising 1 to 3 nitrogen atoms, $Y_1$ is a covalent bond or NH, $R_{9a}$ is H or $C_{1-4}$alkyl, $R_{10a}$ is $C_{1-4}$alkyl, $Z_1$ is O or S.

Where any of $R_1$, $R_2$, $R_3$ and $R_4$ is or comprises $C_{1-4}$alkyl, this is preferably $CH_3$.

Where $R_5$ is 2,2-dihalo-1-cyclopropyl both halogens comprised therein signify F, Cl or Br, particularly Cl or Br, especially Cl; both halogens are preferably identical. Any $C_{1-4}$alkyl substituent of 2,2-dihalo-1-cyclopropyl signifies preferably $CH_3$.

Where $R_5$ is substituted phenyl, it is conveniently mono- or disubstituted. Suitable substituents of phenyl are e.g. $C_{1-4}$alkyl ($CH_3$), $C_{1-4}$alkoxy ($OCH_3$) and halogen (F, Cl, Br).

$R_6$ is preferably $CH_3$.

Where any of $R_7$ and $R_8$ is $C_{1-6}$alkyl, it is conveniently $C_{1-3}$-alkyl, preferably $CH_3$.

Where any of $R_9$, $R'_9$, $R''_9$, $R_{10}$, $R'_{10}$ and $R''_{10}$ is $C_{1-4}$alkyl, it is e.g. $CH_3$.

Where $R_9$ and $R_{10}$, resp. $R'_9$ and $R'_{10}$ resp. $R''_9$ and $R''_{10}$ are linked together and represent alkylene, such alkylene is conveniently unbranched.

Where any of $R_{11}$, $R_{12}$ and $R_{13}$ is $C_{1-4}$alkyl, this is preferably $CH_3$.

Where any of $R_{11}$, $R_{12}$ and $R_{13}$ is halogen, this is preferably Cl or Br, particularly Cl.

Where $R_{14}$ is $C_{1-4}$alkyl, this may be straight or branched and signifies for example $CH_3$.

Where Y is hydrocarbon substituted by halogen, such halogen is conveniently Cl or Br.

Where Y is substituted hydrocarbon, the hydrocarbon signifies preferably $C_{1-6}$alkyl, particularly $C_{1-3}$alkyl.

Where Y is $C_{1-6}$alkyl, unsubstituted, it is preferably $C_{3-5}$-alkyl, particularly unbranched $C_{3-5}$alkyl or 2-methyl-1-butyl.

Where Y is $C_{3-6}$alkenyl, it is preferably $CH=CH-CH_3$.

Where Y is $C_{3-6}$cycloalkyl, it is preferably cyclopropyl or cyclobutyl.

Where Y is a 5-membered heterocycle, this may be aromatic oder hydrogenated; examples of suitable heterocyclic radicals are furyl (e.g. 2-furyl), tetrahydrofuryl, thienyl, isoxazyl and thiadiazolyl. Suitable substituents of such heterocyclic groups are particularly Cl, Br, $CH_3$. Any substituted heterocycle is particularly monosubstituted.

Suitable significances of Az are e.g. pyrazol-1-yl, imidazol-1-yl and 1H-1,2,4-triazol-1-yl.

Where $R_{9a}$ is $C_{1-4}$alkyl, this is especially $CH_3$ or $C_2H_5$.

$R_{10a}$ signifies preferably $CH_3$.

Suitable examples of compounds of formula Ia, wherein Y is esterified $(A)_nZ_1H$ are esters with an alkane carboxylic acids (such as $CH_3COOH$), an alkane sulfonic acid (e.g. $CH_3SO_2OH$), a dialkylsulfamic acid (e.g. $(CH_3)_2NSO_2OH$), a functional derivative of a carbonic acid etc.

Suitable examples of compounds of formula Ia, wherein Y is etherified $(A_1)_nZ_1H$ are e.g. compounds of formula Ia, wherein Y is $(A_1)_nZ_1W$, in which $A_1$, n and $Z_1$ are as defined above and W is a group selected from $C_{1-8}$alkyl (particularly $CH_3$, $C_2H_5$), $C_{3-6}$-alkenyl (particularly $CH_2-CH=CH_2$), $C_{3-6}$alkinyl (particularly $CH_2C\equiv CH$), $C_{1-4}$alkoxy-$C_{1-3}$alkyl (particularly $CH_2OCH_3$), $C_{1-4}$alkylthio-$C_{1-3}$-alkyl (particularly $CH_2SCH_3$) unsubstituted or substituted by halogen (F, Cl, Br) or a pyranyl group.

Preferred compounds of formula Ia have one or more of the following features:

at least one of $R_1$, $R_2$, $R_3$ is different from H, $R_3$ is hydrogen, 3-Cl or 3-Br, $R_1$ is in the 2-position, $R_1$ and $R_2$ are in the 2,6-position, $R_1$ and $R_2$ are selected from H, $CH_3$, Cl and $OCH_3$, $R_1$ and $R_2$ are identical, $R_1$ and $R_2$ are $CH_3$ in the 2,6-position and $R_3$ is H, 3-Cl or 3-Br, X is $CH(R_4)COZR_8$, $N(CH_3)-COOC_{1-6}$alkyl, or 2-oxo-3-oxazolidinyl, Z and Z' are O, $R_8$ is $C_{1-6}$alkyl, $R_8$ is linked with $R_4$ to form $CH_2CH_2$, Y is $CH_2OH$, $CH_2OCH_3$, $CH_2OC_2H_5$, $CH_2O-CH_2-CH=CH_2$, $CH_2O-CH_2-C\equiv CH$, $CH_2-OCH_2OCH_3$, $CH_2OSO_2N(CH_3)_2$, $CH_2Cl$, n-$C_4H_9$, cyclopropyl, $CH=CH-CH_3$, 2-furyl, benzyl, 2-tetrahydrofuryl.

A preferred sub-group of compounds of formula Ia, are compounds of formula Ib

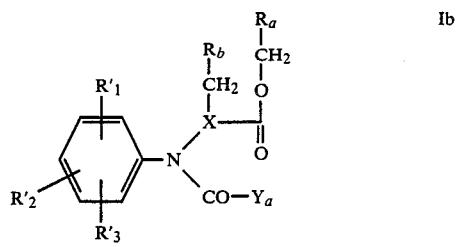

wherein

X is as defined above, either $R_a$ and $R_b$ are both H or together form a covalent bond $Y_a$ is $C_{3-5}$alkenyl; $CH_2OC_{1-5}$alkyl; $CH_2-OC_{3-6}$alkenyl; $CH_2-OC_{3-6}$alkinyl; furyl; benzyl; $CH_2Cl$ or $C_{3-6}$-cycloalkyl, either $R_1'$ and $R_2'$ are both $CH_3$ in the 2- and 6-positions or $R_1'$ is 3-Cl and $R_2'$ is H, and $R_3'$ is H, $CH_3$, Cl or Br.

Where $Y_a$ is $CH_2OC_{1-5}$alkyl, this is preferably $CH_2OCH_3$.

Where $Y_a$ is $C_{3-6}$cycloalkyl, this is preferably cyclopropyl.

Where $Y_a$ is furyl, this is preferably 2-furyl.

Where $Y_a$ is $CH_2OC_{3-6}$alkenyl, this is preferably $CH_2O$allyl or $-CH_2O-(2$-butenyl$)$.

Where $Y_a$ is $CH_2OC_{3-6}$alkinyl, this is preferably $CH_2O(2$-propinyl$)$.

Where in the compounds of formula I $R_3'$ is Cl, Br or $CH_3$ this is preferably in the 3-position, particularly when $R_1'$ and $R_2'$ are 2- and 6-$CH_3$ resp.

Examples of valuable oomycetes controlling fungicidal compounds of formula Ib are those wherein X, $R_a$, $R_b$, $Y_a$, $R_1'$, $R_2'$ and $R_3'$ are (i) CH, H, H, 2-furyl, 2-$CH_3$, 6-$CH_3$ and H resp. (common name furalaxyl)

(ii) CH, H, H, $CH_2-OCH_3$, 2-$CH_3$, 6-$CH_3$ and H resp. (common name metalaxyl)

(iii) CH, H, H, benzyl, 2-$CH_3$, 6-$CH_3$ and H resp. (common name galben)

(iv) CH, covalent bound $(R_a+R_b)$, $CH_2Cl$, 2-$CH_3$, 6-$CH_3$ and H (common name milfuram)

(v) N, covalent bound $(R_a+R_b)$, $CH_2-OCH_3$, 2-$CH_3$, 6-$CH_3$ and H (hereinafter designated compound I)

(vi) N, covalent bound $(R_a+R_b)$, $CH_2-OCH_3$, 2-$CH_3$, 6-$CH_3$, 3-Cl (vii) N, covalent bound $(R_a+R_b)$, $CH_2-OCH_3$, 2-$CH_3$, 6-$CH_3$, 3-Br (viii) CH, covalent bound $(R_a+R_b)$, cyclopropyl, 3-Cl, H and H.

(ix) CH, covalent bound $(R_a+R_b)$, $CH_2OCH_3$, 2-$CH_3$, 6-$CH_3$ and H.

Compounds of formula I are known or may be obtained according to known processes.

Cymoxanil and Phosetyl-Al are also known systemic fungicides having a fungicidal effect against Plasmopara spp and Phytophthora spp.

It has been found, that the use of Cymoxanil or Phosetyl-Al in combination with a compound of formula I particularly one of formula Ia, more particularly one of formula Ib, e.g. one of the compounds (i) to (ix) indicated above, surprisingly and substantially enhances the effectiveness of the latter against such fungi, and vice versa. The risk of fungi developing resistance against oomycetes controlling having the structure element of formula I is also significantly decreased when using them in association with Cymoxanil or Phosetyl-Al. Moreover, the method of the invention is also surprisingly active against acylalanine resistant field strains of Phytophthora spp and Plasmopara spp as indicated i.a. by a significant decrease of the factor of resistance (the ratio of the fungicidal activity at the 90% level against resistant and sensitive strains). The term "acylalanine resistant field strains" as used herein means oomycetes that developed resistant against acylalanine type fungicides (see e.g. Resistant to acylalanine-type fungicides in Peronosporales, Phytopathology 71(5) 558 (1981). Finally, the method of the invention is effective against a wider spectrum of fungi than that that can be combatted with the active ingredients of this method when used solely.

Accordingly, the invention provides an improved method of combatting fungi, particularly fungi of the class Oomycetes such as Phytophthora spp., Plasmopara spp., Peronospora spp., Pseudo-peronospora spp., Sclerophthora spp., Bremia spp. and Pythium spp., in crop locus, especially in grapevines, tomato, hops, cacao, tobacco, potato and lettuce cultures, and an eucalyptus locus which comprises applying to the locus, in admixture or separately, a fungicidally effective aggregate amount of a compound of formula I and Cymoxanil or Phosetyl-Al.

The term crop as used herein is intended to embrace any desired plant growth.

Preferably the compounds of formula I are applied at a rate of 100–400 g/ha, particularly 150–300 g/ha, e.g. 200 g/ha in association with 40–160 g/ha, particularly 60–120 g/ha, e.g. 80 g/ha Cymoxanil or 750–2500 g/ha, particularly 1000–2000 g/ha, e.g. 1500 g/ha Phosetyl-Al.

Other pesticides e.g. fungicides, bactericides, insecticides, acaricides, herbicides or plant growth regulating agents may be used in addition to the above associated active ingredients, to enhance the activity of the association of the invention or to widen its spectrum of activity; it is particularly advantageous to use an additional contact fungicide in the method of the invention.

Contact fungicides particularly indicated for use together with the association of the invention are one or more fungicides selected from a copper fungicide, e.g. cuprous oxide, copper (II) oxychloride, cupric hydroxide, copper (II) calcium sulphate, copper (II) calcium oxychloride, Bordeaux mixture or Burgundy mixture; captan; dichlofluanid; folpet; mancozeb; maneb; zineb; chlorothalonil; propineb and dithianon or mixture thereof. Such additional contact fungicide(s) may in general be applied at a rate of 200–2000 g/ha. Mancozeb is particularly appropriate for use in the method of this invention. It has an additional synergistic effect on the compound of formula I combinations with Cymoxanil or Phosetyl-Al.

The invention also provides fungicidal compositions comprising a compound of formula I and Cymoxanil or Phosetyl-Al.

In the composition of the invention the weight ratio compound of formula I: Cymoxanil lies preferably in the range of 10:1 to 1:3, more preferably 5:1 to 1:1, particularly 4:1 to 2:1 e.g. 2.5:1. The synergistic effect is evident from the various experimental data in the tables hereinafter, where synergism is i.a. illustrated for the weight ratio compound of formula I: Cymoxanil in the range 1:0.3 to 1:3.

In the compositions of the invention the weight ratio compound of formula I: Phosetyl-Al lies preferably in the range of 1:25 to 1:2, more preferably in the range of 1:15 to 1:3, particularly 1:10 to 1:5 e.g. 1:7.

Where the compositions of the invention comprise additionally a contact fungicide, the weight ratio compound of formula I: contact fungicide lies preferably in the range of 1:2 to 1:10, and where Mancozeb, Folpet, Captan or Maneb are used, more preferably 1:4 to 1:9, particularly 1:5 to 1:8 e.g. 1:7. It is particularly advantageous to incorporate Mancozeb in the compositions of the invention.

The composition of the invention may be employed in any conventional form, for example in the form of a twin pack, an instant granulate, a flowable or a wettable powder in association with fungicidally acceptable diluents. Such compositions may be produced in conventional manner, e.g. by mixing the active ingredients with a diluent (carrier) and other formulating ingredients such as surfactants.

The term diluents as used herein means any liquid or solid agriculturally acceptable material which may be added to the active constituents to bring it in an easier or improved applicable form, respectively to a usable or desirable strength of activity. It can for example be talc, kaolin, diatomaceous earth, xylene, or water.

Particularly formulations to be applied in spraying forms such as water dispersible concentrates or wettable powders may contain surfactants such as wetting and dispersing agents, e.g. the condensation product of formaldehyde with naphthalene sulphonate, an alkylarylsulphonate, a lignin sulphonate, a fatty alkyl sulphate, an ethoxylated alkylphenol and an ethoxylated fatty alcohol.

In general, the formulations include from 0.01 to 90% by weight of active agent from 0 to 20% fungicidally acceptable surfactant and 10 to 99.99% solid or liquid diluent(s), the active agent consisting of at least one compound of formula I together with Cymoxanil or Phosetyl-Al, and optionally other active agents, particularly contact fungicides. Concentrate forms of compositions generally contain between about 2 and 80%, preferably between about 5 and 70% by weight of active agent. Application forms of formulation may for example contain from 0.01 to 20% by weight, preferably from 0.01 to 5% by weight of active agent.

The invention is illustrated by the following Examples wherein parts and percentages are by weight and temperatures are in °C.

TEST A

Fungicidal effect against *Phytophthora infestans* strains resistant against acylalanine type fungicides Yound potted tomato or potato plants (3–5 leaf stage) are sprayed with an aqueous spray liquid of
mixture A,
    containing 0.05 to 0.0002% compound of formula I
    and 0.05 to 0.0002% CYMOXANIL,
or mixture B,
    containing 0.05 to 0.0002% compound of formula I
    and 2 to 0.2% Phosetyl-Al
or mixture C, containing 0.05 to 0.0002% compound of formula I and 0.2 to 0.003% of a contact fungicide such as Mancozeb, Folpet, Captan, dichlofluanid, Maneb or copper fungicides.

Two hours (or 4, 8, 16, 32 or 64 hours later) the treated plants or leaves thereof are washed vigorously, e.g. by simulated rain washing at a rain rate of 10-50 mm/hour. Two hours after the washing procedure, the treated plants or leaves are inoculated with a spore suspension ($10^5$ sporangia/ml) of Phytophthora infestans strains that developed resistance against compounds of formula I. The plants are then transferred to a tent providing 100% relative atmospheric humidity at an ambient temperature of 16° and a day length of 16 hours. Disease control is evaluated 4–5 days thereafter, by comparing the treated plants (leaves) with untreated, similarly inoculated plants (leaves). Where, with the mixtures A and B complete control of the fungal infestation is observed, the degree of fungicidal activity provided by mixture C is significantly less pronounced. Similar results are obtained in grape vines against Plasmopara viticola strains which are resistant against acylalanine type fungicides.

TEST B

Synergistic activity

In this test, the fungicidal acitvity provided by the compounds of formula I, CYMOXANIL or Phosetyl-Al alone, is compared with the activity provided by a compound of formula I when used in association with CYMOXANIL or Phosetyl-Al. The presence of an eventual synergistic effect between two active ingredients is then established with the aid of the Colby equation $$p = A + B - \frac{A \times B}{100}$$

wherein A and B are the fungicidal activities of the active ingredients when used alone and p is the fungicidal activity that theoretically would have been obtained with the mixture if there was no interaction between the active ingredients. If p is lower than the experimentally established fungicidal effect, there is synergism.

Young potted potato plants are sprayed with an aqueous spray liquid containing either a compound of formula I, CYMOXANIL or Phosetyl-Al alone or in the association according to the invention. The compounds of formula I and CYMOXANIL are applied in concentrations of 0.0125 to 0.00002%, Phosetyl-Al in concentrations of 0.8 to 0.0125%, until the run-off.

Two hours later, the treated plants are inoculated with a spore suspension of *Phytophthora infestans* and the plants are then transferred to a tent providing 100% relative atmospheric humidity at an ambient temperature of 16° C. and a day length of 16 hours. Disease control is evaluated 4-5 days later by comparing the treated plants with untreated, similarly inoculated plants. Analogous tests are run using grape plants infested with *Plasmopara viticola*.

A more than additive effect is obtained as illustrated in the following tables, in which Comp. is Compound I, Cym is Cymoxanil, Phos. is Phosetyl-Al, M is Mancozeb, the underlined figures are p(Colby) and the non-underlined figures are the experimentally established fungicidal effect.

TABLE I

Phytophthora/Tomato

| Cym. | Comp. 0 | 2 | 8 | 32 | ppm |
|---|---|---|---|---|---|
| 0 | 0 | 60 | 80 | 100 | |
| 2 | 10 | 80 $\underline{64}$ | 90 $\underline{82}$ | 100 | |
| 8 | 40 | 100 $\underline{76}$ | 100 $\underline{88}$ | 100 | |
| 32 ppm | 60 | 100 $\underline{84}$ | 100 $\underline{92}$ | 100 | |

TABLE II

Phytophthora/Tomato

| Cym. | Comp. 0 | 0.2 | 0.6 | 1.8 | 5.4 | ppm |
|---|---|---|---|---|---|---|
| 0 | 0 | 0 | 20 | 40 | 70 | |
| 0.2 | 0 | 10 $\underline{0}$ | 30 $\underline{20}$ | 50 $\underline{40}$ | 90 $\underline{70}$ | |
| 0.6 | 0 | 20 $\underline{0}$ | 30 $\underline{20}$ | 60 $\underline{40}$ | 90 $\underline{70}$ | |
| 1.8 | 20 | 20 $\underline{20}$ | 40 $\underline{36}$ | 65 $\underline{52}$ | 100 $\underline{76}$ | |
| 5.4 ppm | 40 | 40 $\underline{40}$ | 60 $\underline{52}$ | 80 $\underline{64}$ | 100 $\underline{82}$ | |

TABLE III

Phytophthora/Tomato

| Phos. | Comp. 0 | 2 | 8 | 32 | ppm |
|---|---|---|---|---|---|
| 0 | 0 | 60 | 80 | 100 | |
| 125 | 20 | 70 $\underline{68}$ | 90 $\underline{84}$ | 100 | |
| 500 | 50 | 90 $\underline{80}$ | 100 $\underline{90}$ | 100 | |
| 2000 ppm | 70 | 100 $\underline{88}$ | 100 $\underline{94}$ | 100 | |

TABLE IV

Phytophthora/Potato

| Phos. | Comp. 0 | 2 | 8 | 32 | ppm |
|---|---|---|---|---|---|
| 0 | 0 | 50 | 80 | 100 | |
| 125 | 10 | 60 $\underline{54}$ | 80 $\underline{82}$ | 100 | |
| 500 | 30 | 80 $\underline{65}$ | 100 $\underline{86}$ | 100 | |
| 2000 ppm | 80 | 100 $\underline{90}$ | 100 $\underline{96}$ | 100 | |

TABLE V

Plasmopara/grape vine

| Cym. | Comp. 0 | 0.2 | 0.6 | 1.8 | 5.4 | ppm |
|---|---|---|---|---|---|---|
| 0 | 0 | 0 | 30 | 50 | 60 | |
| 0.2 | 0 | 30 $\underline{0}$ | 40 $\underline{30}$ | 55 $\underline{50}$ | 70 $\underline{60}$ | |
| 0.6 | 20 | 40 $\underline{20}$ | 50 $\underline{44}$ | 60 $\underline{60}$ | 80 $\underline{68}$ | |
| 1.8 | 50 | 50 $\underline{50}$ | 80 $\underline{65}$ | 90 $\underline{75}$ | 100 $\underline{80}$ | |

TABLE V-continued

Plasmopara/grape vine

| Cym. | Comp. 0 | 0.2 | 0.6 | 1.8 | 5.4 |
|---|---|---|---|---|---|
| 5.4 ppm | 60 | 60$_{60}$ | 90$_{72}$ | 100$_{80}$ | 100$_{84}$ |

TABLE VI

Plasmopara/grape vine

| Phos. | Comp. 0 | 0.2 | 0.6 | 1.8 | 5.4 ppm |
|---|---|---|---|---|---|
| 0 | 0 | 0 | 0 | 40 | 50 |
| 10 | 10 | 10$_{10}$ | 30$_{28}$ | 50$_{46}$ | 60$_{55}$ |
| 30 | 20 | 20$_{20}$ | 40$_{36}$ | 60$_{52}$ | 70$_{60}$ |
| 90 | 40 | 40$_{40}$ | 60$_{52}$ | 70$_{64}$ | 80$_{70}$ |
| 270 ppm | 50 | 50$_{50}$ | 70$_{60}$ | 80$_{70}$ | 90$_{75}$ |

TABLE VII

Phytophthora/Tomato

| | Comp. 0 | 0.125 | 0.375 | 1.13 | 3.38 ppm |
|---|---|---|---|---|---|
| | | | M | | |
| Cym. | 0 | 0.9 | 2.7 | 8.1 | 24.3 ppm |
| 0 | 0 | 10 | 20 | 40 | 60 |
| 0.1 | 0 | 2.5$_{10}$ | 30$_{20}$ | 50$_{40}$ | 80$_{60}$ |
| 0.3 | 0 | 35$_{10}$ | 40$_{20}$ | 60$_{40}$ | 90$_{60}$ |
| 0.9 | 20 | 45$_{28}$ | 50$_{36}$ | 70$_{52}$ | 100$_{68}$ |
| 2.7 ppm | 35 | 50$_{41}$ | 55$_{48}$ | 100$_{61}$ | 100$_{74}$ |

TABLE VIII

Plasmopara/grape vine

| | Comp. 0 | 0.125 | 0.375 | 1.13 | 3.38 ppm |
|---|---|---|---|---|---|
| | | | M | | |
| Cym. | | 0.9 | 2.7 | 8.1 | 24.3 ppm |
| 0 | 0 | 30 | 50 | 60 | 70 |
| 0.1 | 0 | 30$_{30}$ | 60$_{50}$ | 70$_{60}$ | 100$_{70}$ |
| 0.3 | 20 | 50$_{44}$ | 70$_{60}$ | 80$_{68}$ | 100$_{76}$ |
| 0.9 | 40 | 60$_{58}$ | 80$_{70}$ | 100$_{76}$ | 100$_{82}$ |
| 2.7 ppm | 60 | 80$_{72}$ | 100$_{80}$ | 100$_{84}$ | 100$_{88}$ |

Based on the results in Table I–VIII—which indicate a synergism—the factor of synergism can be calculated with the aid of the Wadley equations:

$$EC\ 90\ (theor.) = \frac{a + b + \ldots}{\frac{a}{EC\ 90} + \frac{b}{EC\ 90}}$$

and $$SF = \frac{EC\ 90\ (theor.)}{EC\ 90\ (exp.)}$$

wherein a, b, etc. are the weight ratios at which the active ingredients are used in the mixture; EC 90, EC 90 (exp.) and EC' (theor.) the concentrations allowing a 90% fungicidal control resp. of the active ingredient when used alone as determined by experiment, of the tested composition as determined by experiment and of the tested composition as calculated. SF is the factor of synergism (in case of synergism it is $\geq 1$).

The factor of synergism (SF) found with mixtures of Compound I/Cymoxanil and of Compound I/Cymaoxanil/Mancozeb resp. tested on tomato (*Phytophthora infestans*) and grape vine (*Plasmopara viticola*) under greenhouse conditions, calculated according to Wadley, are given:

TABLE IX

| | Tomato (Phyt.) EC 90[2] | | | Grape vine (Plasm.) EC 90[2] | | |
|---|---|---|---|---|---|---|
| | theor. | exp. | SF[2] | theor. | exp. | SF[2] |
| Comp./Cym[*] | | | | | | |
| 1:0 | — | 17 | | — | 19 | |
| 1:0.3 | 21 | 7 | 3.0 | 23 | 11 | 2.1 |
| 1:1 | 31 | 10 | 3.1 | 26 | 5 | 5.2 |
| 1:3 | 49 | 16 | 3.1 | 30 | 4 | 7.5 |
| 0:1 | | 125 | | | 36 | |
| Comp./Cym/M | | | | | | |
| 1:0.3:7 | 69 | 29 | 2.4 | 49 | 16 | 3.1 |
| 1:2.4:7 | 76 | 32 | 2.4 | 46 | 6 | 7.7 |

[*]weight ratio
[2]see Wadley

| | Formulation Examples (Wettable powders) | | | | | | | |
|---|---|---|---|---|---|---|---|---|
| | A | B | C | D | E | F | G | H |
| | % by weight | | | | | | | |
| Compound of formula I (e.g. Compound 1) | 8. | 10 | 7 | 10 | 40 | 7 | 10 | 25 |
| CYMOXANIL | 3.2 | 5 | — | 10 | 24 | — | 5 | 10 |
| Phosetyl-Al | — | — | 50 | — | — | 50 | — | — |
| Contact fungicide e.g. | | | | | | | | |
| Mancozeb | 56 | 25 | — | — | | | 25 | |
| Copper (II) oxychloride | — | 10 | — | — | | | 17.5 | |
| Copper (II) calcium sulphate | — | 5 | — | — | | | 18.5 | |
| Folpet | — | — | 23 | 30 | | | — | |
| Surfactant: | | | | | | | | |
| Wetting agent (e.g. Na alkyl naphthalene sulphonate) | 1 | 1 | 1 | 1 | 1 | 1 | 1 | 1 |
| Dispersing agent (e.g. Na lignin sulphonate) | 5 | 5 | 5 | 5 | 5 | 5 | 5 | 5 |
| Diluent: | | | | | | | | |
| Silica | 5 | 5 | 5 | 5 | 5 | 5 | 5 | 5 |
| Kaolin | 21.8 | 34 | 9 | 39 | 25 | 28 | 13 | 54 |
| Prussian blue | — | — | — | — | — | 4 | — | — |

The formulations are obtained by mixing the components, subsequently milling the mixture and a second mixing in conventional manner.

In general, the active ingredients are used in technical form. An example of a formulation comprising technical active ingredients is as follows:

Example J

| Compound I technical (95%) | 10.5% |
|---|---|
| Cymoxanil - technical (95%) | 5.3% |

-continued

| Mancozeb - technical (80%) | 31.3% |
| Copperoxy (II) chloride (57% Cu) | 17.5% |
| Copper (II) calcium sulphate (27% Cu) | 18.7% |
| Surfactant and Silica | 11.0% |
| Kaolin | 5.7% |

Example K—Flowable 440 g/l

| 4.2% w/w | Compound I techn. 95% |
| 1.7% w/w | Cymoxanil techn. 95% |
| 35.0% w/w | Mancozeb techn. 80% |
| 4.0% w/w | Surfactant |
| 6.0% w/w | 1,2-Propylene glycol (Anti-freezing) |
| 0.3% w/w | Sticker |
| 0.5% w/w | Stabilisator (e.g. citric acid) |
| 48.3% w/w | Water |
| 100.0% w/w | |

The formulation is produced by mixing the components, wet grinding and mixing.

Example L—Granules 67% w/w WG

| 8.4% w/w | Compound I techn. 95% |
| 3.4% w/w | Cymoxanil techn. 95% |
| 70.0% w/w | Mancozeb techn. 80% |
| 10.0% w/w | Dispersing/binding agent (e.g. Na—lignin-sulfonate) |
| 7.7% w/w | Diluent (e.g. kaolin) |
| 0.5% w/w | Stabilisator (e.g. citric acid). |

The formulation is produced by mixing and grinding the components followed by pan-granulation or fluid bed-granulation.

The granules disperse well in water, forming a sprayable suspension.

What is claimed is:

1. A fungicidal composition comprising a component (a) of the formula I,

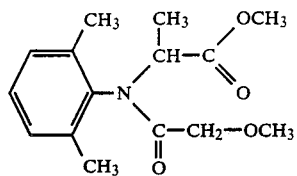

and a component (b) which is cymoxanil; the weight ratio of component (a) to component (b) being in the range of from 10:1 to 1:1.

2. A composition according to claim 1 in which the weight ratio of component (a) to component (b) is within the range of from 5:1 to 1:1.

3. A composition according to claim 2 in which the weight ratio of component (a) to component (b) is 4:1 to 2:1.

4. The method of combatting Oomycetes fungus in a crop locus comprising applying to said locus a fungicidally effective amount of a compostion of claim 1.

5. The method according to claim 4 in which the Oomycetes fungus to be combatted is resistant to said component (a).

6. The method according to claim 5 in which component (a) is applied at a rate of from 100 to 400 g/ha and component (b) is applied at a rate from 40 to 160 g/ha.

7. The method according to claim 4 in which the weight ratio of component (a) to component (b) is within the range from 5:1 to 1:1.

8. The method according to claim 7 in which component (a) is applied at a rate of from 150 to 300 g/ha and component (b) is applied at a rate of from 60 to 120 g/ha.

9. The method according to claim 5 in which the weight ratio of component (a) to component (b) is within the range from 5:1 to 1:1.

10. The method according to claim 9 in which component (a) is applied at a rate of from 150 to 300 g/ha and component (b) is applied at a rate of from 60 to 120 g/ha.

11. The method according to claim 4 in which the fungus to be combatted is Phytophthora spp or Plasmopara spp.

12. The method according to claim 5 in which the fungus to be combatted is Phytophthora spp or Plasmopara spp.

* * * * *